United States Patent
Inagaki et al.

(10) Patent No.: US 11,352,308 B2
(45) Date of Patent: Jun. 7, 2022

(54) COMPOUND AND SEMICONDUCTOR MATERIAL CONTAINING SAME

(71) Applicant: DIC Corporation, Tokyo (JP)

(72) Inventors: Sho Inagaki, Sakura (JP); Aya Ishizuka, Sakura (JP); Hideki Etori, Sakura (JP)

(73) Assignee: DIC Corporation, Tokyo (JP)

( * ) Notice: Subject to any disclaimer, the term of this patent is extended or adjusted under 35 U.S.C. 154(b) by 952 days.

(21) Appl. No.: 16/081,201

(22) PCT Filed: Mar. 14, 2017

(86) PCT No.: PCT/JP2017/010130
§ 371 (c)(1),
(2) Date: Aug. 30, 2018

(87) PCT Pub. No.: WO2017/159658
PCT Pub. Date: Sep. 21, 2017

(65) Prior Publication Data
US 2019/0077732 A1   Mar. 14, 2019

(30) Foreign Application Priority Data
Mar. 17, 2016   (JP) .............................. JP2016-053866

(51) Int. Cl.
*C07C 15/28* (2006.01)
*C07D 233/64* (2006.01)
(Continued)

(52) U.S. Cl.
CPC ............ *C07C 15/28* (2013.01); *C07C 43/275* (2013.01); *C07D 213/30* (2013.01);
(Continued)

(58) Field of Classification Search
CPC ............. H01L 51/0545; H01L 51/0004; H01L 51/0008; H01L 51/0058; H01L 51/0067;
(Continued)

(56) References Cited

U.S. PATENT DOCUMENTS

2008/0001123 A1*  1/2008  Inoue .................. H01L 51/0054
                                                                      252/301.16
2010/0025670 A1   2/2010  Saito et al.
(Continued)

FOREIGN PATENT DOCUMENTS

CN        104035294 A    9/2014
JP        2004-107257 A  4/2004
(Continued)

OTHER PUBLICATIONS

Inoue et al., "Organic thin-film transistors based on anthracene oligomers", May 15, 2004, Journal of Applied Physics, vol. 95, No. 10, pp. 5795-5799. (Year: 2004).*
(Continued)

*Primary Examiner* — Matthew E. Hoban
*Assistant Examiner* — Lynne Edmondson
(74) *Attorney, Agent, or Firm* — Locke Lord LLP; James E. Armstrong, IV; Nicholas J. DiCeglie, Jr.

(57) ABSTRACT

There is provided a compound which provides a semiconductor material. The compound is represented by General Formula (1)

General Formula (1)

(Continued)

wherein Ar represents an aryl group which may have a substituent or a heteroaryl group which may have a substituent, and $R^1$ represents an acyclic alkyl group having 1 to 20 carbon atoms wherein hydrogen atom in the alkyl group may be replaced by a halogeno group, a nitrile group or an aryl group, and —$CH_2$— in the alkyl group may be replaced by —O—, —R'C=CR'—, —CO—, —OCO—, —COO—, —S—, —$SO_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms.

6 Claims, 1 Drawing Sheet

(51) Int. Cl.
| | |
|---|---|
| *H01L 29/786* | (2006.01) |
| *H01L 51/05* | (2006.01) |
| *C09D 11/00* | (2014.01) |
| *C07C 43/275* | (2006.01) |
| *C07D 213/30* | (2006.01) |
| *C07D 471/06* | (2006.01) |
| *H01L 51/00* | (2006.01) |
| *C07B 61/00* | (2006.01) |

(52) U.S. Cl.
CPC ......... *C07D 233/64* (2013.01); *C07D 471/06* (2013.01); *C09D 11/00* (2013.01); *H01L 29/786* (2013.01); *H01L 51/0004* (2013.01); *H01L 51/0008* (2013.01); *H01L 51/0058* (2013.01); *H01L 51/0067* (2013.01); *H01L 51/0072* (2013.01); *H01L 51/05* (2013.01); *H01L 51/0545* (2013.01); *C07B 61/00* (2013.01)

(58) Field of Classification Search
CPC ... H01L 51/0072; H01L 29/786; C07C 15/28; C07C 43/275; C07C 1/322; C07D 213/30; C07D 233/64; C07D 471/06
See application file for complete search history.

(56) References Cited

U.S. PATENT DOCUMENTS

| | | |
|---|---|---|
| 2014/0255836 A1 | 9/2014 | Nakata et al. |
| 2014/0255837 A1 | 9/2014 | Nakata et al. |
| 2015/0023913 A1 | 1/2015 | Hewawasam et al. |

FOREIGN PATENT DOCUMENTS

| | | |
|---|---|---|
| JP | 2007-502812 A | 2/2007 |
| JP | 2010-205749 A | 9/2010 |
| JP | 2014-197173 A | 10/2014 |
| TW | 200845444 A | 11/2008 |
| WO | 03/095445 A1 | 11/2003 |
| WO | 2008/069060 A1 | 6/2008 |
| WO | 2012/121393 A1 | 9/2012 |
| WO | 2015/005901 A1 | 1/2015 |

OTHER PUBLICATIONS

Y. Inoue et al., "Organic thin-film transistors based on anthracene oligomers," Journal of Applied Physics vol. 95, No. 10 pp. 5795-5799, May 15, 2004. (cited in the Oct. 10, 2020 Office Action issued for CN201780008026.2).
Office Action dated Oct. 10, 2020, issued for Chinese Patent Application No. 201780008026.2.
Supplementary European Search Report dated Jul. 12, 2019, issued for European Patent Application No. 17766657.5.
Office Action issued for Korean Patent Application.
Youji Inoue et al., "Organic thin-film transistors based on anthracene oligomers," Journal of Applied Physics, May 15, 2004, vol. 95, No. 10, pp. 5795-5799. (cited in the ISR).
Takashi Kaneko et al., "Transformation from preformed racemic helical poly(phenylacetylene)s to the enantioenriched helical polymers by chiral solvation, followed by removal of the chiral solvents," Polymer Journal, 2012, vol. 44, pp. 327-333. (cited in the ISR).
Jie Liu et al., "Thin film field-effect transistors of 2,6-diphenylanthracene (DPA)," Chem Commun., Vo., 51, 2015, pp. 11777-11779. (discussed in the spec).
International Search Report dated May 30, 2017, issued for PCT/JP2017/010130.

\* cited by examiner

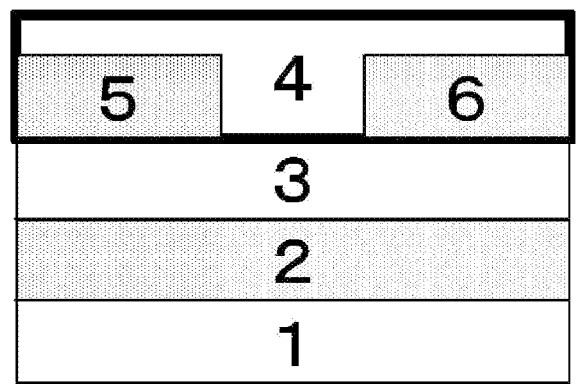

COMPOUND AND SEMICONDUCTOR MATERIAL CONTAINING SAME

TECHNICAL FIELD

The present invention relates to a novel compound and a semiconductor material including the same.

BACKGROUND ART

A transistor in which amorphous silicon or polycrystalline silicon is used as a semiconductor material has been widely used as a switching element for a liquid crystal display device, an organic EL display device and other display devices. However, a transistor using the silicon materials requires a high-temperature heat treatment process in the manufacturing thereof, and therefore, due to a problem of heat resistance, the transistor cannot be applied to a next generation flexible display device in which a plastic substrate is supposed to be used. In order to solve this problem, an organic transistor in which an organic compound is used as a semiconductor material instead of silicon has been proposed. Hereinafter, a semiconductor material using an organic compound may be referred to as an organic semiconductor material.

The organic semiconductor material can be applied to a plastic substrate with poor heat resistance and has been expected to be applied to a flexible display device and further expected to be applied to a flexible electronic device such as a light-weight flexible electronic tag or sensor, since the use of the organic semiconductor material as an ink makes it possible to forma film at low temperature by a coating method (which may hereinafter be referred to as a wet film forming method) or a printing method (which may hereinafter be referred to as a wet film forming method). Meanwhile, an organic semiconductor had a problem in that, since the mobility (which is an index showing semiconductor properties the unit of which is $cm^2/Vs$) was low as compared with that of the silicon semiconductor, a response speed of the transistor was slow and thereby it was difficult to put it into practical use. However, with respect to this problem, in recent years, organic semiconductor materials, the mobility of which exceeds that of amorphous silicon, have been developed.

For example, NPL 1 discloses a compound having a 2,6-diphenylanthracene unit, and discloses that the mobility of a transistor fabricated using this compound achieves 14.8 $cm^2/Vs$ (wherein the semiconductor layer is formed by a vacuum film forming method, not a wet film forming method), demonstrating that an anthracene derivative has high potential, from a viewpoint of obtaining high semiconductor properties. On the other hand, this compound has a problem with a low solubility, which makes it difficult to use the compound for a wet film forming method.

PTL 1 discloses a compound having a 2,6-substituted anthracene unit and discloses that a hydrogen atom, an aliphatic hydrocarbon group having C1 to C20, a thienyl group or other functional groups can be used as a substitute thereof, but does not disclose the compound according to the present invention.

PTL 2 discloses a compound represented by (side chain)-(aromatic unit)-(aromatic unit) as a general formula, but does not disclose the compound according to the present invention.

PTL 3 discloses a compound having an anthracene skeleton, but does not disclose the compound according to the present invention.

CITATION LIST

Non Patent Literature

[NPL 1] Chemical Communications, 2015, vol. 51, p. 11777

Patent Literature

[PTL 1] WO 2003/095445
[PTL 2] WO 2012/121393
[PTL 3] JP-T-2007/502812

SUMMARY OF INVENTION

Technical Problem

As described above, organic semiconductor materials are characterized by being capable of allowing the formation of semiconductor devices such as transistors by a wet film forming method. Therefore, an object of the present invention is to provide a semiconductor material with which a semiconductor device exhibiting high mobility can be fabricated by a wet film forming method and to provide a compound which can provide such a semiconductor material.

Solution to Problem

In order to achieve the above-described object, the present inventors have repeatedly conducted intensive studies, found that an anthracene derivative having a substituent having a specified chemical structure allows the fabrication of a semiconductor device exhibiting high mobility by a wet film forming method, and thereby completed the present invention.

That is, the present invention is configured as follows.

1. A compound represented by General Formula (1), exclusive of compounds (1-1), (1-2), (1-3), (1-4), (1-5) and (1-6) below.

[Chem. 1]

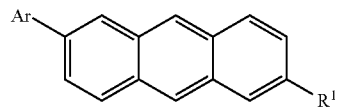

(1)

In the formula, Ar represents an aryl group which may have a substituent or a heteroaryl group which may have a substituent, and $R^1$ represents an acyclic alkyl group having 1 to 20 carbon atoms wherein a hydrogen atom in the alkyl group may be replaced by a halogeno group, a nitrile group or an aryl group, and —$CH_2$— in the alkyl group may be replaced by —O—, —R'C=CR'—, —CO—, —OCO—, —COO—, —S—, —$SO_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms.

[Chem. 2]

(1-1)
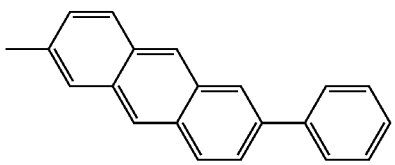

(1-2)
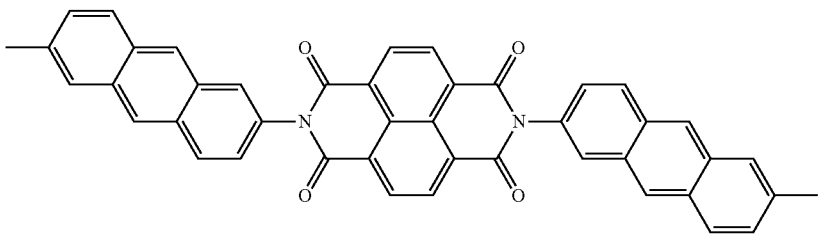

(1-3)
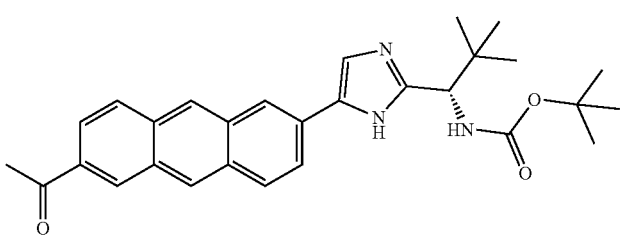

[Chem. 3]

(1-4)
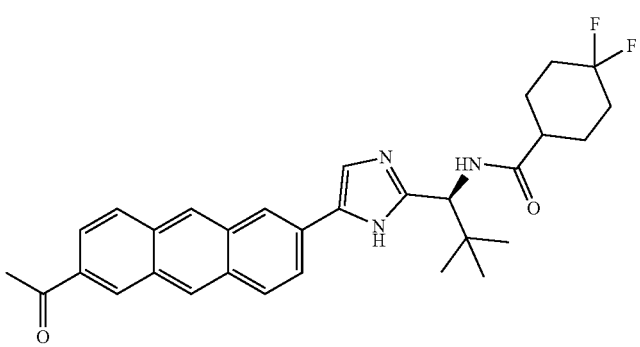

(1-5)
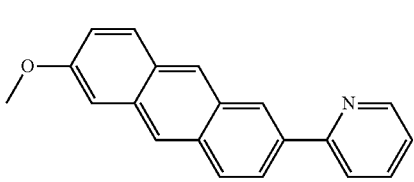

(1-6)
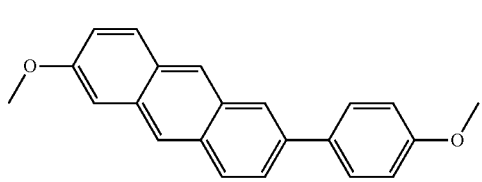

2. A semiconductor material including the compound according to item 1.

3. An ink including the compound according to item 1.

4. A semiconductor film including the compound according to item 1.

5. A semiconductor device including a semiconductor layer including the compound according to item 1.

6. A transistor including a semiconductor layer including the compound according to item 1.

Advantageous Effects of Invention

According to the present invention, it is possible to provide a semiconductor device exhibiting high mobility, which is fabricated by a wet film forming method.

BRIEF DESCRIPTION OF DRAWING

FIG. 1 is a schematic cross section view of a bottom gate bottom contact (BGBC) type transistor.

DESCRIPTION OF EMBODIMENTS (Compound of Present Invention)

Hereinafter, a compound of the present invention will be described. The compound of the present invention is an anthracene derivative represented by General Formula (1).

[Chem. 4]

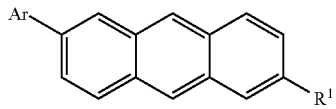
(1)

In the formula, Ar represents an aryl group which may have a substituent or a heteroaryl group which may have a substituent, and $R^1$ represents an acyclic alkyl group having 1 to 20 carbon atoms wherein hydrogen atom in the alkyl group may be substituted with a halogeno group, a nitrile group or an aryl group, and —CH$_2$— in the alkyl group may be replaced by —O—, —R'C=CR'—, —CO—, —OCO—, —COO—, —S—, —SO$_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms.

Ar of the compound represented by General Formula (1) will be described.

Ar is not particularly limited, as long as it is an aryl group which may be substituted or a heteroaryl group which may be substituted, and examples thereof include a monocyclic or polycyclic aryl group such as a phenyl group, a substituted phenyl group, a naphthyl group, a substituted naphthyl group, an azulenyl group, a substituted azulenyl group, an anthryl group, a substituted anthryl group, a phenanthryl group, a substituted phenanthryl group, an acenaphthylenyl group, a substituted acenaphthylenyl group, an acenaphthenyl group, a substituted acenaphthenyl group, a fluorenyl group, a substituted fluorenyl group, a naphthacenyl group, a substituted naphthacenyl group, a pyrenyl group, a substituted pyrenyl group, a chrysenyl group, a substituted chrysenyl group, a perylenyl group, a substituted perylenyl group, a monovalent functional group derived from biphenyl or substituted biphenyl, a monovalent functional group derived from p-terphenyl or substituted p-terphenyl, or a monovalent functional group derived from p-quaterphenyl or substituted p-quaterphenyl; and a monocyclic or polycyclic heteroaryl group such as a pyrrolyl group, a substituted pyrrolyl group, an imidazolyl group, a substituted imidazolyl group, a pyrazolyl group, a substituted pyrazolyl group, a triazolyl group, a substituted triazolyl group, a tetrazolyl group, a substituted tetrazolyl group, a furyl group, a substituted furyl group, a thienyl group, a substituted thienyl group, an oxazolyl group, a substituted oxazolyl group, a thiazolyl group, a substituted thiazolyl group, an oxadiazolyl group, a substituted oxadiazolyl group, a thiadiazolyl group, a substituted thiadiazolyl group, a pyrrolothiazolyl group, a substituted pyrrolothiazolyl group, a thienothienyl group, a substituted thienothienyl group, an indolyl group, a substituted indolyl group, an indolinyl group, a substituted indolinyl group, an indolizinyl group, a substituted indolizinyl group, a pyrrolopyridazinyl group, a substituted pyrrolopyridazinyl group, a benzotriazolyl group, a substituted benzotriazole, a benzofuryl group, a substituted benzofuryl group, a benzothienyl group, a substituted benzothienyl group, a benzoxazolyl group, a substituted benzoxazolyl group, a carbazolyl group, a substituted carbazolyl group, a monovalent functional group derived from dibenzofuran or substituted dibenzofuran, a monovalent functional group derived from dibenzothiophene or substituted dibenzothiophene, a pyridyl group, a substituted pyridyl group, a pyridazinyl group, a substituted pyridazinyl group, a pyrimidinyl group, a substituted pyrimidinyl group, a pyrazinyl group, a substituted pyrazinyl group, a quinolinyl group, a substituted quinolinyl group, an isoquinolinyl group, a substituted isoquinolinyl group, a benzoquinolinyl group, a substituted benzoquinolinyl group, a monovalent functional group derived from bithiophene or substituted bithiophene, a monovalent functional group derived from terthiophene or substituted terthiophene, a monovalent functional group derived from quarter thiophene or substituted quarter thiophene.

The substituent of Ar is not particularly limited, as long as it is a conventionally known substituent as a substituent of an aromatic compound, and examples thereof include a hydrogen atom, a halogeno group, a nitro group, a nitrile group, an acyclic or cyclic alkyl group having 1 to 20 carbon atoms (wherein hydrogen atom in the alkyl group may be substituted with a halogeno group, a nitrile group or an aryl group, and —CH$_2$— in the alkyl group may be replaced by —O—, —R'C=CR'—, —CO—, —OCO—, —COO—, —S—, —SO$_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms), an aryl group (wherein the aryl group may be substituted with a halogeno group, a nitro group, a nitrile group, an acyclic or cyclic alkyl group having 1 to 20 carbon atoms or an aryl group, and —CH$_2$— in the alkyl group may be replaced by —O—, —CR"=CR"—, —CO—, —OCO—, —COO—, —S—, —SO$_2$—, —SO—, —NH—, —NR"— or —C≡C— provided that, with respect to each of an oxygen atom, a sulfur atom and a nitrogen atom, the same atoms are not directly bonded to each other, wherein R" represents an acyclic or cyclic alkyl group having 1 to 20 carbon atoms), and other well-known substituents.

From a viewpoint of exhibiting the high mobility, the substituent of Ar is preferably a hydrogen atom or an acyclic or cyclic alkyl group having 1 to 20 carbon atoms, more preferably a hydrogen atom or an acyclic alkyl group having 1 to 20 carbon atoms, and even more preferably a hydrogen atom or a linear alkyl group having 1 to 20 carbon atoms.

From a viewpoint of exhibiting the high mobility, among the above-described groups, Ar is preferably a group represented by General Formula (2),

[Chem. 5]

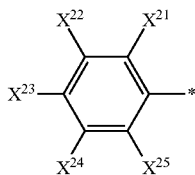
(2)

wherein $X^{21}$ to $X^{25}$ represent a hydrogen atom or an acyclic or cyclic alkyl group having 1 to 20 carbon atoms and * represents a bonding position as a monovalent substituent; and more preferably a group represented by General Formula (3),

[Chem. 6]

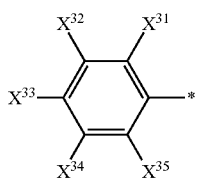

(3)

wherein $X^{31}$, $X^{32}$, $X^{34}$ and $X^{35}$ represent a hydrogen atom, $X^{33}$ represents a hydrogen atom or a linear alkyl group having 1 to 20 carbon atoms, and * represents a bonding position as a monovalent substituent.

Next, $R^1$ of the compound represented by General Formula (1) will be described.

$R^1$ is an acyclic alkyl group having 1 to 20 carbon atoms wherein hydrogen atom in the alkyl group may be substituted with a halogeno group, a nitrile group or an aryl group, and —$CH_2$— in the alkyl group may be replaced by —O—, —R'C=CR'—, —CO—, —OCO—, —COO—, —S—, —$SO_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms.

Specifically, examples of the acyclic alkyl group having 1 to 20 carbon atoms (wherein hydrogen atom in the alkyl group may be substituted with a halogeno group, a nitrile group or an aryl group, and —$CH_2$— in the alkyl group may be replaced by —O—, —R'C=CR'—, —CO—, —OCO—, —COO—, —S—, —$SO_2$—, —SO—, —NH—, —NR'— or —C≡C— provided that, with respect to each of an oxygen atom, a sulfur atom and a nitrogen atom, the same atoms are not directly bonded to each other, wherein R' represents an acyclic or cyclic alkyl group having 1 to 20 carbon atoms) include the following:

a linear alkyl group having 1 to 20 carbon atoms, the linear alkyl group referred to as (A-1);
an alkoxy group having 1 to 19 carbon atoms, the alkoxy group referred to as (A-2);
an alkoxyalkyl group having 2 to 19 carbon atoms, the alkoxyalkyl group referred to as (A-3);
an alkenyl group having 2 to 20 carbon atoms, the alkenyl group referred to as (A-4);
an alkanoyl group having 2 to 20 carbon atoms, the alkanoyl group referred to as (A-5);
an alkanoylalkyl group having 3 to 20 carbon atoms, the alkanoylalkyl group referred to as (A-6);
an alkoxycarbonyl group having 2 to 20 carbon atoms, the alkoxycarbonyl group referred to as (A-7);
an alkanoyloxy group having 2 to 20 carbon atoms, the alkanoyloxy group referred to as (A-8);
an alkylsulfanyl group having 1 to 19 carbon atoms, the alkylsulfanyl group referred to as (A-9);
an alkylsulfanylalkyl group having 2 to 19 carbon atoms, the alkylsulfanylalkyl group referred to as (A-10);
an alkylsulfonyl group having 1 to 19 carbon atoms, the alkylsulfonyl group referred to as (A-11);
an alkylsulfonylalkyl group having 2 to 19 carbon atoms, the alkylsulfonylalkyl group referred to as (A-12);
an alkylsulfinyl group having 1 to 19 carbon atoms, the alkylsulfinyl group referred to as (A-13);
an alkylsulfinylalkyl group having 2 to 19 carbon atoms, the alkylsulfinylalkyl group referred to as (A-14);
an alkylamino group having 1 to 19 carbon atoms, the alkylamino group referred to as (A-15);
an alkylaminoalkyl group having 2 to 19 carbon atoms, the alkylaminoalkyl group referred to as (A-16); and
an alkynyl group having 2 to 20 carbon atoms, the alkynyl group referred to as (A-17).

Among the above-described (A-1) to (A-17), from the viewpoint of improving the film forming property and the mobility of the compound of the present invention, (A-1), (A-2), (A-3), (A-4), (A-9), (A-10) or (A-17) is preferable, and in order to obtain a compound having higher mobility, (A-1) is more preferable.

From the viewpoint of exhibiting the high mobility, (A-1) is preferably a linear alkyl group having 3 to 12 carbon atoms, and more preferably a linear alkyl group having 6 to 10 carbon atoms.

Specific examples of (A-1) include a linear alkyl group such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-eicosyl group and other linear alkyl groups.

Examples of the specific compound of the present invention include the following compounds, and the compound of the present invention is not limited thereto. As the specific compound of the present invention, examples where Ar is a phenyl group and $R^1$ is an alkyl group having 1 to 20 carbon atoms are given as follows.

[Chem. 7]

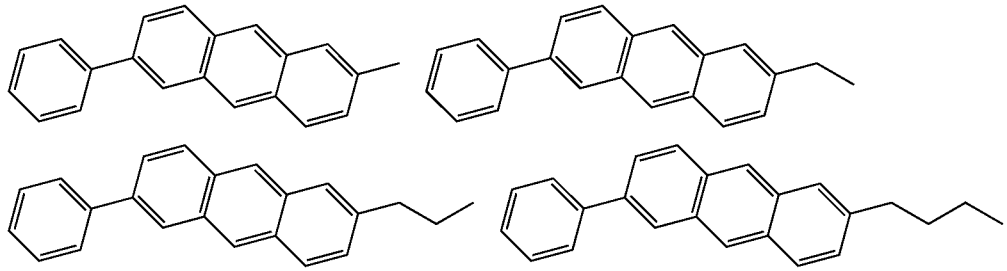

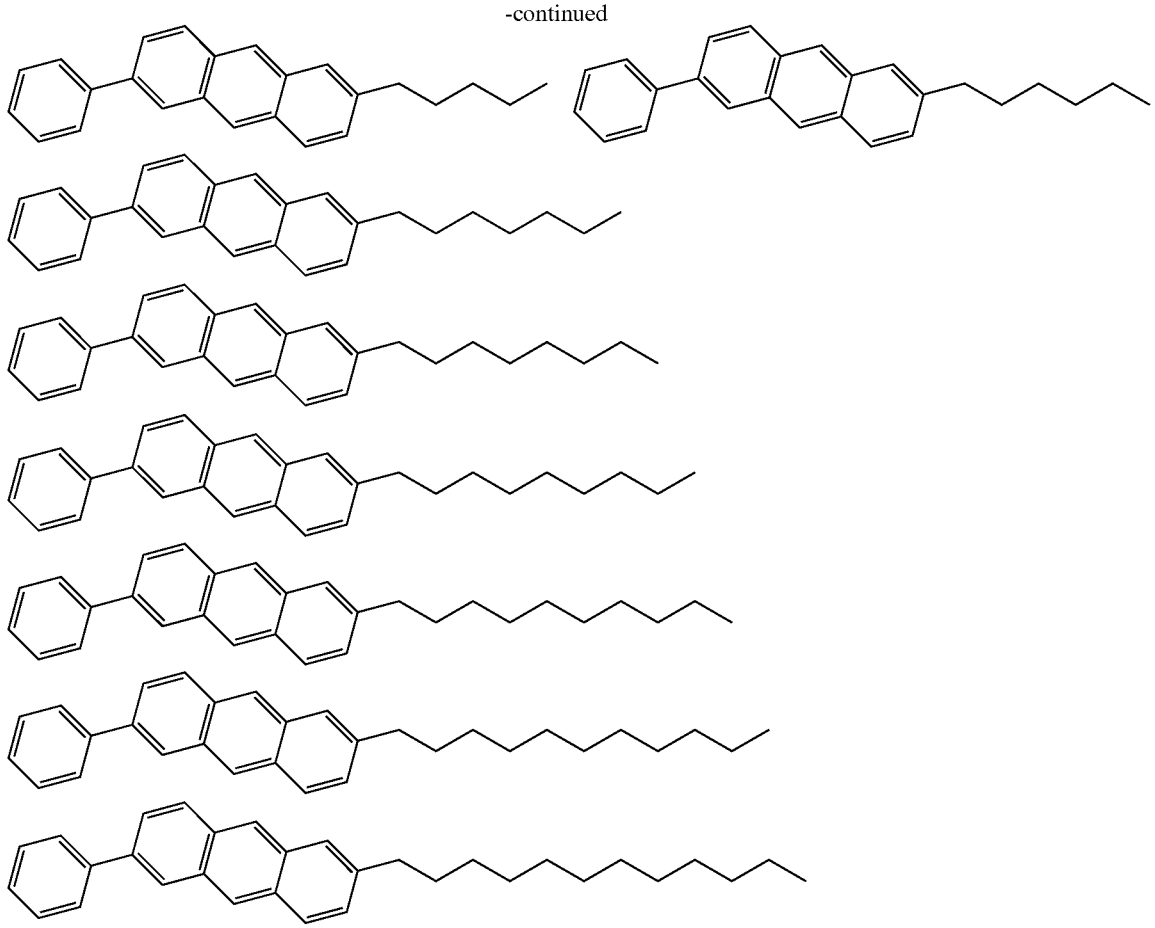
As the specific compound of the present invention, examples where Ar is a 4-alkylphenyl group and $R^1$ is an alkyl group having 1 to 20 carbon atoms are given as follows.
[Chem. 8]
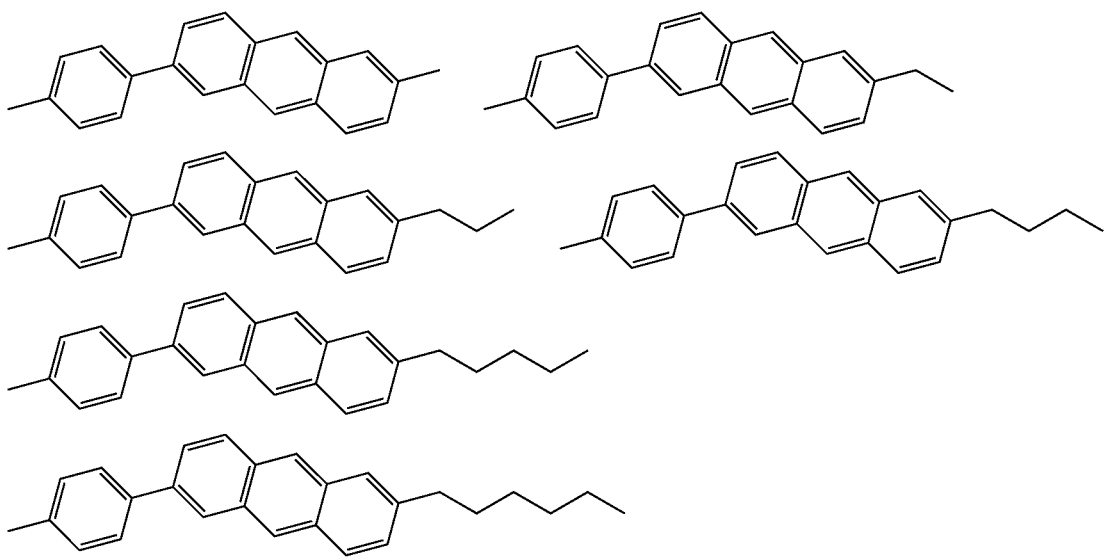

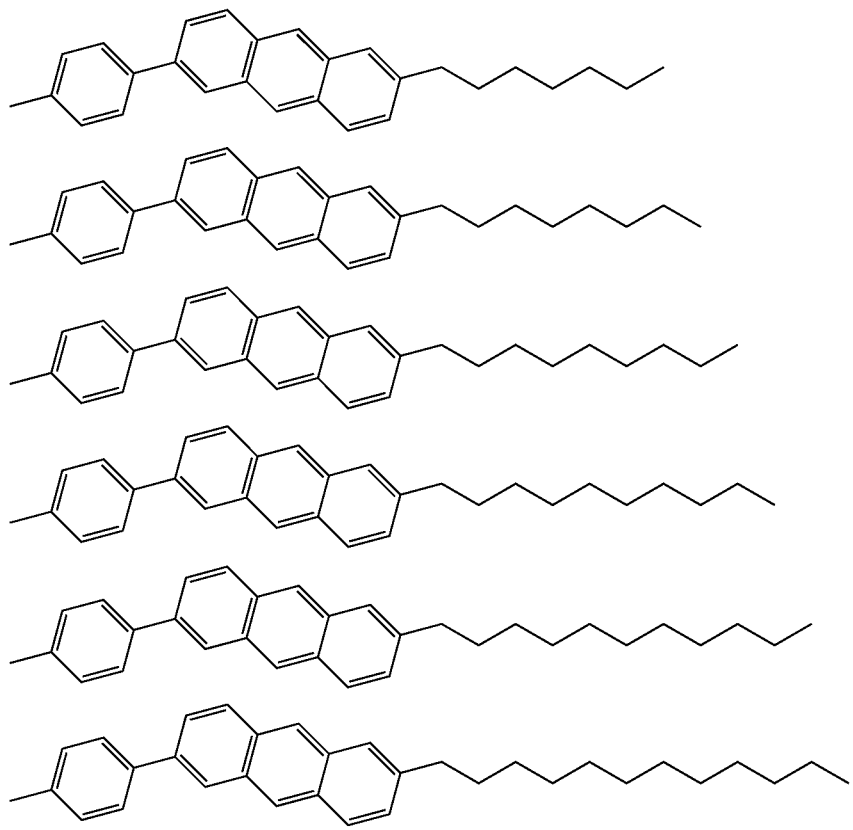
[Chem. 9]
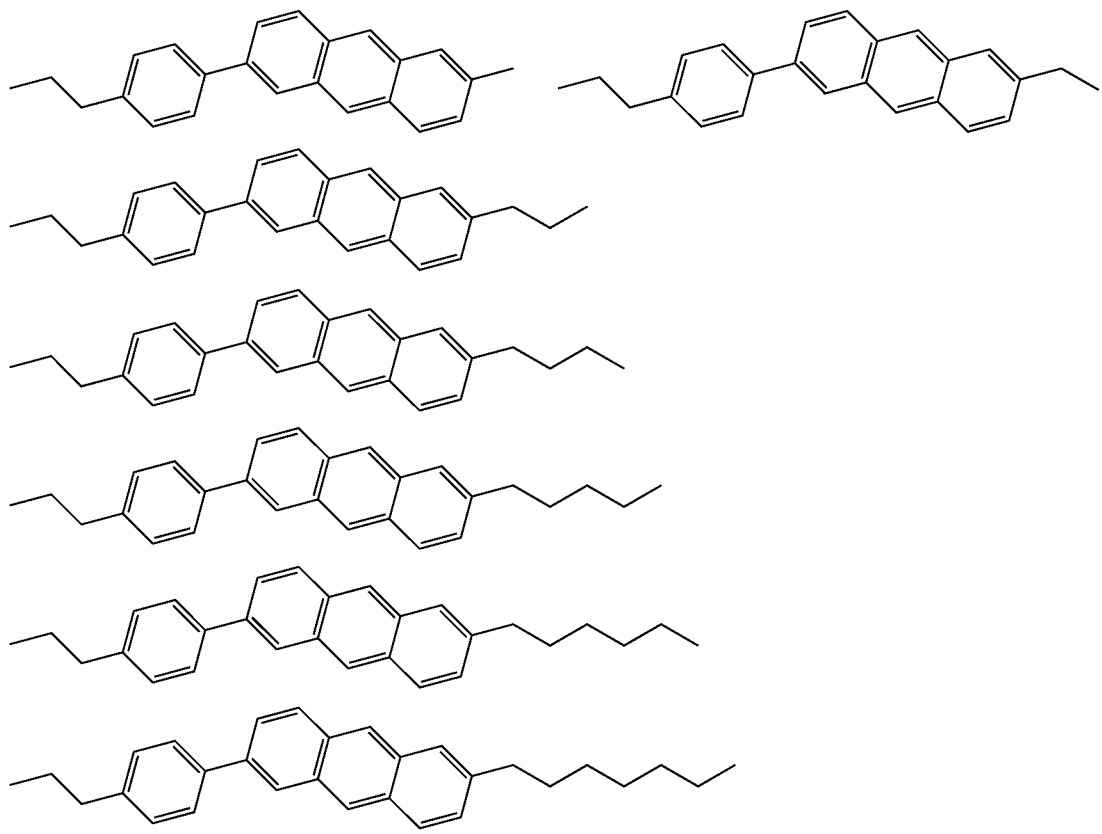

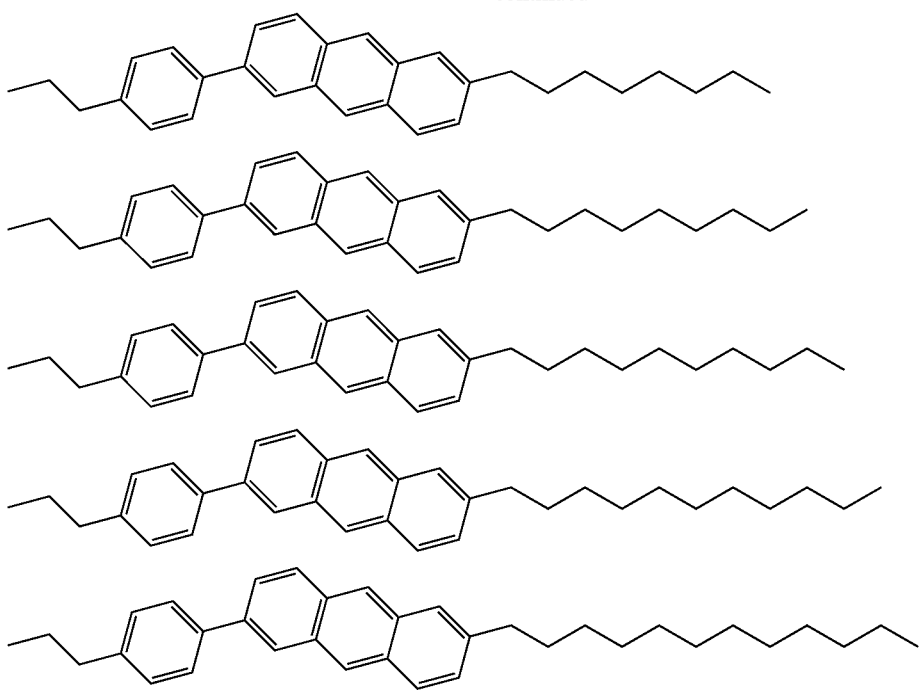
[Chem. 10]
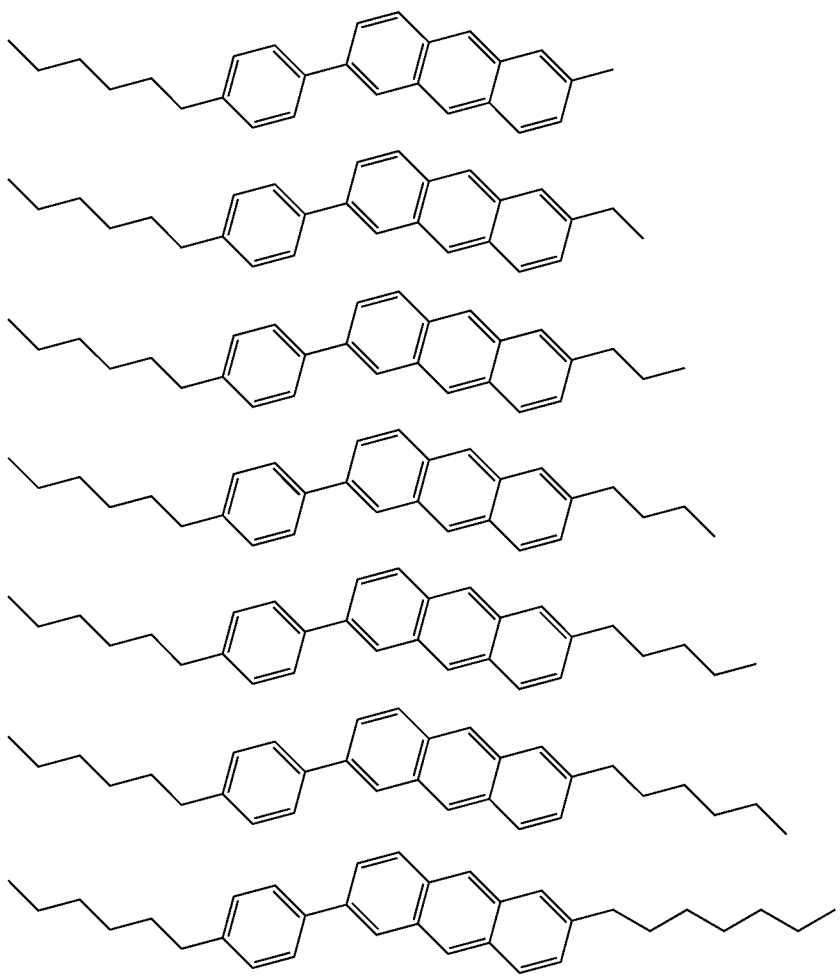

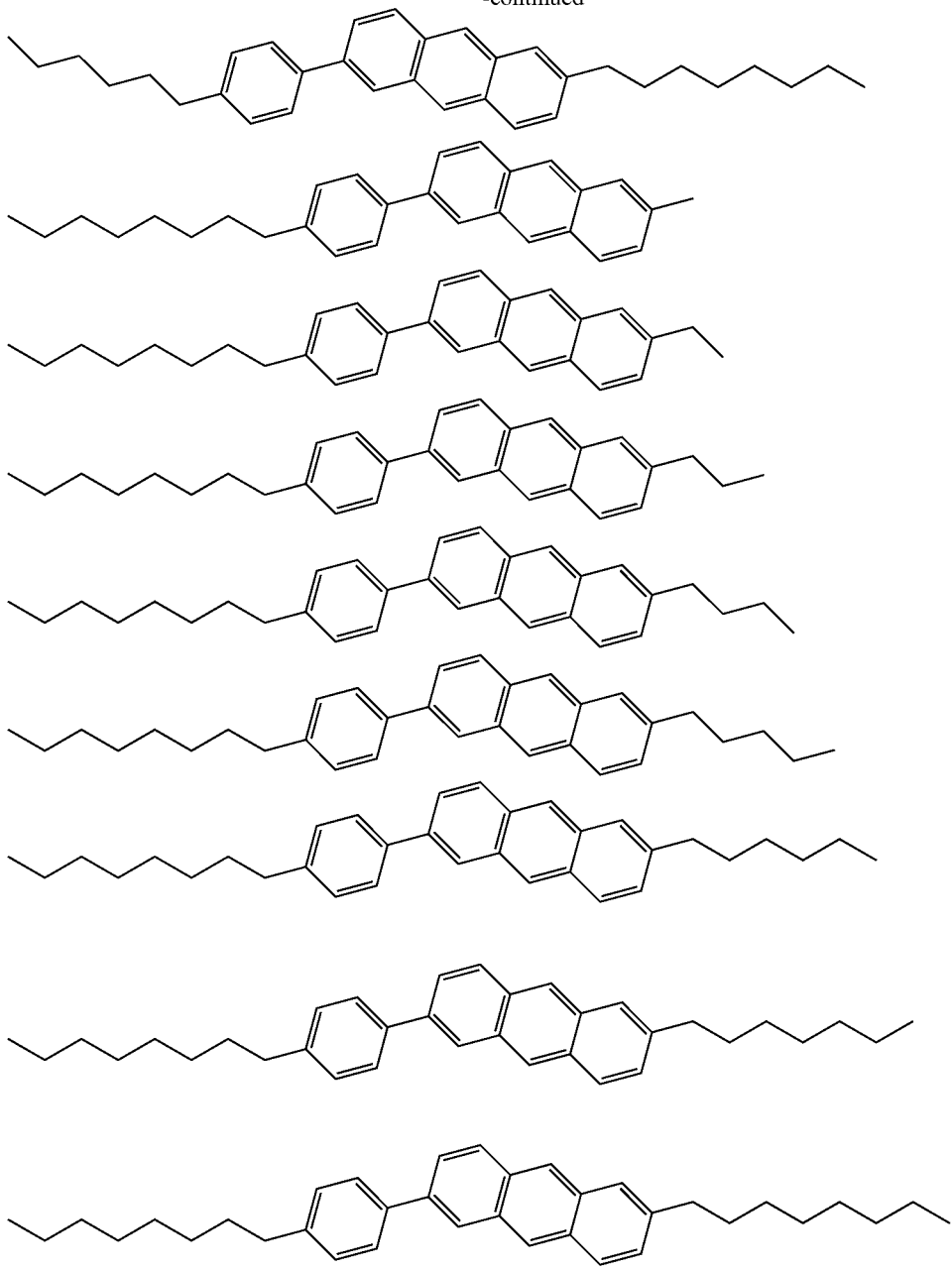

(Preparation of Compound of Present Invention)

A method of preparing the compound of the present invention will be described.

The method of preparing the compound of the present invention is not particularly limited, as long as it is a method capable of providing the compound of the present invention. As described below, the compound of the present invention can be prepared by combining conventionally known synthetic reactions.

The method of preparing the compound of the present invention will be described by using a reaction scheme (S1). The reaction scheme (S1) is an example of the preparing method in a case where $R^1$ in the compound represented by General Formula (1) is an alkyl group having 1 to 20 carbon atoms.

[Chem. 11]

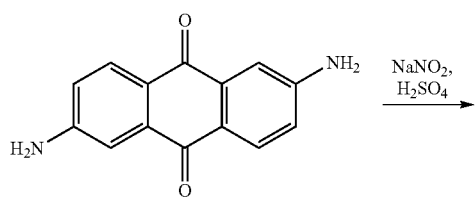

-continued

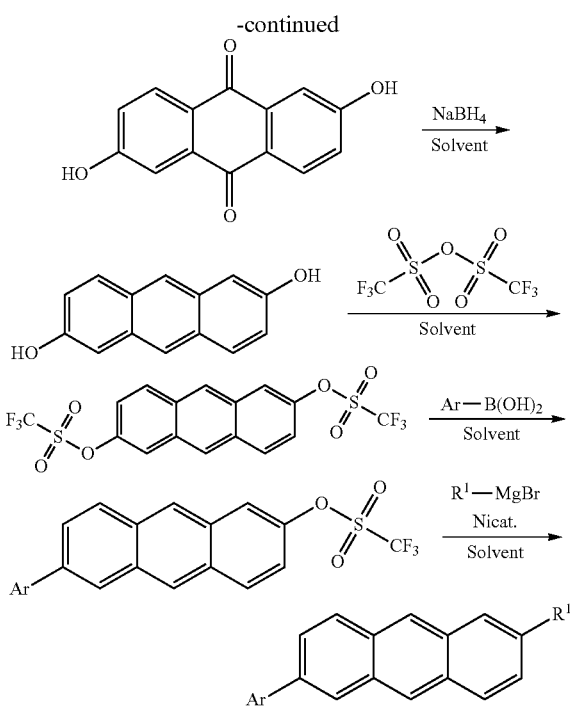

(S1)

In the formula, Ar is identical to Ar of General Formula (1).

First, sodium nitrite is allowed to react with 2,6-diaminoanthraquinone to be dihydroxylated (first step), followed by the reduction with sodium borohydride (second step). Then, trifluoromethanesulfonic anhydride is allowed to react to introduce bis(trifluoromethanesulfonyl) group (third step), followed by the Suzuki-Miyaura coupling with aryl boronic acid (Ar—B(OH)$_2$) to introduce Ar (fourth step). Finally, the Kumada-Tamao coupling using a Grignard reagent (R$^1$—MgBr) is conducted, and a target compound Ar-(anthracene)-R$^1$ is obtained (fifth step).

(Semiconductor Material of Present Invention)

A semiconductor material of the present invention will be described.

The compound of the present invention can be used as a semiconductor material for a semiconductor device. A form of the semiconductor material of the present invention is not particularly limited, as long as it is a form capable of providing a semiconductor device, and examples thereof include solid form such as single crystal, polycrystal, powder, amorphous film, polycrystalline film, single crystal film or thin film; and liquid form such as solution, dispersion liquid, coating solution or ink. Among these, a coating solution or an ink is preferable, considering that the organic semiconductor material is characterized in that it allows the fabrication of a semiconductor device by a wet film forming method.

The semiconductor material of the present invention may contain a material other than the compound of the present invention within a range where the provided semiconductor device exhibits desired semiconductor properties.

(Ink of Present Invention)

An ink of the present invention will be described.

The ink of the present invention is a material for forming a semiconductor film having the compound of the present invention by a wet film forming method, is a material for forming a semiconductor layer having the compound of the present invention and included in the semiconductor device of the present invention fabricated by a wet film forming method, and is a material providing the semiconductor device of the present invention fabricated by a wet film forming method.

The ink of the present invention includes a solvent which can dissolve or disperse the compound of the present invention, in addition to the compound of the present invention.

Such a solvent is not particularly limited, as long as it can dissolve or disperse the compound of the present invention, and examples thereof include an ester solvent such as methyl acetate, normal propyl acetate, isopropyl acetate, propylene glycol monomethyl ether acetate (PGMAc), 3-methoxy-3-methyl-butyl acetate, ethoxyethyl propionate (EEP) or propylene carbonate;

an alcohol solvent such as methanol, ethanol, 1-propanol, 2-propanol, 1-butanol, 2-methyl-1-butanol, 3-methoxy-3-methyl-1-butanol, 1,3-butanediol, 1-pentanol, 4-methyl-2-pentanol, 1-hexanol, cyclohexanol or an industrial higher alcohol such as DIADOL Series (product name, Mitsubishi Chemical Corporation);

a hydrocarbon solvent such as pentane, n-hexane, hexane, cyclohexane, methylcyclohexane, n-octane, n-decane, toluene or xylene; a chlorinated solvent such as dichloromethane or chloroform;

an aromatic solvent such as benzene, toluene, cumene, n-propylbenzene, n-butylbenzene, n-pentylbenzene, o-xylene, m-xylene, p-xylene, p-cymene, 1,4-diethylbenzene, mesitylene, 1,3,5-triethylbenzene, anisole, 2-methylanisole, 3-methylanisole, 4-methylanisole, 2,5-dimethylanisole, 1,3-dimethoxybenzene, 3,5-dimethoxytoluene, 2,4-dimethylanisole, phenetole, methyl benzoate, ethyl benzoate, propyl benzoate, butyl benzoate, chlorobenzene, o-dichlorobenzene, trichlorobenzene, tetralin, 1,5-dimethyltetralin, 1-methylnaphthalene or an industrial aromatic solvent such as SOLVESSO 100, SOLVESSO 150 or the like (product name, Exxon Mobil Corporation);

an ether solvent such as tetrahydrofuran, 2-methyltetrahydrofuran, dioxane, ethylene glycol diethyl ether (monoglyme), diglyme, triglyme, ethylene glycol monomethyl ether (cellosolve), ethyl cellosolve, propio cellosolve, butyl cellosolve, phenyl cellosolve, diethylene glycol methyl ether, diethylene glycol ethyl ether, diethylene glycol propyl ether, diethylene glycol butyl ether, benzyl ethyl ether, ethyl phenyl ether, diphenyl ether, methyl-t-butyl ether, cyclopentyl methyl ether, cyclohexyl methyl ether benzonitrile propylene glycol monomethyl ether, propylene glycol monoethyl ether, propylene glycol monopropyl ether, propylene glycol tertiary butyl ether, dipropylene glycol monomethyl ether, ethylene glycol butyl ether, ethylene glycol ethyl ether, ethylene glycol methyl ether, diethylene glycol butyl ether or diethylene glycol ethyl ether;

a ketone solvent such as acetone, methyl ethyl ketone, cyclohexanone, 2-hexanone, 2-heptanone, 3-heptanone, acetophenone, propiophenone, butyrophenone or cyclohexanone; and an aprotic polar solvent such as N,N-dimethylformamide, dimethylsulfoxide, diethylformamide or N-methyl-2-pyrrolidone.

The solvent used in the ink of the present invention may be used singly or two or more kinds thereof may be used in combination.

Depending on the purpose, the ink of the present invention may include a semiconductor material other than the compound of the present invention. Examples of such a semiconductor material include an electron donating material, an electron accepting material, an electron transporting material, a hole transporting material, a light emitting material, a light absorbing material and other well-known semiconductor materials.

In addition, the ink of the present invention may include a polymer compound or a resin, a body or extender pigment, a surfactant, a release agent and other additive materials. These materials are added to the ink of the present invention, if necessary, in order to add printability and film shape retaining properties.

A resin which can be included in the ink of the present invention is not particularly limited, as long as it is a conventionally known insulating resin, and examples thereof include a polymer compound such as cyanoethyl pullulan, cellulose acetate propionate (CAP), cellulose triacetate (TAC), polyarylate (PAR), polyimide, polyester, polyethylene terephthalate (PET), polyethylene naphthalate (PEN), polyether imide (PEI), polyether ether ketone (PEEK), polyether sulfone (PES), polyvinylidene chloride (PVDC), polyvinyl chloride (PVC), polycarbonate (PC), polycycloolefin, polystyrene and a polystyrene derivative, polytetrafluoroethylene (PTFE), a polyparaxylylene derivative such as PARYLENE SERIES (product name), polyvinyl alcohol (PVA), polyvinyl phenol (PVP), polyphenylene sulfide (PPS), polymethyl methacrylate (PMMA), acrylic resin, amorphous fluororesin such as CYTOP SERIES (product name, Asahi Glass Co., Ltd.), alkyd resin, urethane resin, epoxy resin, an electron beam curable resin such as electron beam curable acrylic resin or electron beam curable methacrylic resin, phenoxy resin, phenol resin, fluororesin, unsaturated polyester resin, polyimide resin, polyvinyl phenol resin, melamine resin, or a UV curable resin such as UV curable acrylic resin or UV curable methacrylic resin. The resin included in the ink of the present invention may be one kind or two or more kinds thereof.

The concentration of the resin in the ink is not particularly limited, as long as it is in a range where the semiconductor device fabricated using the ink of the present invention exhibits desired semiconductor properties, and is generally preferably 1 wt % to 10 wt % and more preferably 3 wt % to 7 wt %.

The body or extender pigment which can be included in the ink of the present invention is not particularly limited, as long as it is a conventionally known electrical insulating inorganic particulate matter or a conventionally known electrical insulating pigment, and examples thereof include an inorganic particulate matter such as AEROSIL SERIES (product name, Evonik Industries), SYLYSIA, SYLOPHOBIC, SYLOPUTE, SYLOPAGE, SYLOPURE, SYLOSPHERE, SYLOMASK, SYLWELL, FUJI BALLOON (all, product names, Fuji Sylsia Chemical Ltd.), PMA-ST, IPA-ST (both, product names, Nissan Chemical Industries, Ltd.), NANOBIC 3600 SERIES, or NANOBIC 3800 SERIES (both series, product names, BYK); and a pigment such as EXCEDIC BLUE 0565, EXCEDIC RED 0759, EXCEDIC YELLOW 0599, EXCEDIC GREEN 0358, or EXCEDIC YELLOW 0648 (all, product names, DIC Corporation).

The body or extender pigment included in the ink of the present invention may be used alone or in combination of two or more kinds thereof.

The concentration of the body or extender pigment in the ink is not particularly limited, as long as it is in a range where the semiconductor device fabricated using the ink of the present invention exhibits desired semiconductor properties, and is generally preferably in a range of 0 wt % to 20 wt % as an effective component.

The surfactant which can be included in the ink of the present invention is not particularly limited, as long as it is a conventionally known electrical insulating surfactant, and examples thereof include a hydrocarbon type surfactant, a silicone type surfactant, and a fluorine type surfactant. Among these, a fluorosurfactant having a linear perfluoroalkyl group with a chain length equal to or greater than C6, such as MEGAFACE F-482, MEGAFACE F-470 (R-08), MEGAFACE F-472 SF, MEGAFACE R-30, MEGAFACE F-484, MEGAFACE F-486, MEGAFACE F-172 D or MEGAFACE F178 RM (all, product names, DIC Corporation) is preferable.

The surfactant included in the ink of the present invention may be used alone or in combination of two or more kinds thereof.

The concentration of the surfactant in the ink is not particularly limited, as long as it is in a range where the semiconductor device fabricated using the ink of the present invention exhibits desired semiconductor properties, and is generally preferably in a range of 0.01 wt % to 5.00 wt % as an effective component and more preferably in a range of 0.05 wt % to 1.00 wt % as an effective component.

The release agent which can be included in the ink of the present invention is not particularly limited, as long as it is a conventionally known electrical insulating silicone compound, and examples thereof include dimethyl silicone oil, dimethyl silicone rubber, silicone resin, organic modified silicone oil, methyl phenyl silicone oil, long chain alkyl modified silicone oil, a mixture of organofluoride and silicone polymer and fluorinated silicone. Among these, GLANOL SERIES (product name, Kyoeisha Chemical Co., Ltd.) and KF-96L SERIES (product name, Shin-Etsu Chemical Co., Ltd.) are preferable, from a viewpoint of release properties and compatibility with the resin.

The release agent included in the ink of the present invention may be used alone or in combination of two or more kinds thereof.

The concentration of the release agent in the ink is not particularly limited, as long as it is in a range where the semiconductor device fabricated using the ink of the present invention exhibits desired semiconductor properties, and is generally preferably in a range of 0.0 wt % to 5.0 wt % as an effective component, and more preferably in a range of 0.0 wt % to 3.0 wt % as an effective component.

In addition, if needed, the ink of the present invention can include a leveling agent, a dispersing agent, a defoaming agent and any other additive agents, as an optional component.

The concentration of the compound of the present invention in the ink is not particularly limited, as long as it is in a range where the semiconductor device fabricated using the ink of the present invention exhibits desired semiconductor properties, and is generally preferably in a range of 0.01 wt % to 20.00 wt %, more preferably in a range of 0.05 wt % to 10.00 wt %, and even more preferably in a range of 0.10 wt % to 10.00 wt %.

(Semiconductor Device of Present Invention)

The semiconductor device of the present invention will be described.

The semiconductor device of the present invention is not particularly limited, as long as it is a semiconductor device including a semiconductor layer formed using the compound of the present invention, and can include a diode; a thyristor; a photodiode; a photoelectric transducer such as a solar cell or a light receiving element; a transistor such as a field effect type transistor, a static induction type transistor, a bipolar transistor or a thin film transistor; a light emitting device such as an organic EL device or a light emitting transistor; a sensor such as a temperature sensor, a chemical sensor, a gas sensor, a humidity sensor, a radiation sensor, a biosensor, a blood sensor, an immunosensor, an artificial retina, a taste sensor or a pressure sensor; a logic circuit unit such as an inverter, a ring oscillator or a RFID; and other semiconductor devices.

(Transistor of Present Invention)

A transistor of the present invention will be described.

The transistor is a semiconductor device which is made of a gate electrode, a gate insulator, a source electrode, a drain electrode and a semiconductor layer, and is classified into various types according to how each electrode and each layer are configured geometrically.

The configuration of the transistor of the present invention is not particularly limited, as long as it includes the compound of the present invention as a semiconductor layer, and examples thereof include a bottom gate bottom contact (hereinafter, abbreviated as BGBC) type transistor, a bottom gate top contact (hereinafter, abbreviated as BGTC) type transistor, a top gate bottom contact (hereinafter, abbreviated as TGBC) type transistor, a top gate top contact (hereinafter, abbreviated as TGTC) type transistor, a metal base organic transistor (hereinafter, abbreviated as MBOT), and a static induction transistor (hereinafter, abbreviated as SIT).

Next, a substrate which is a constituent element of the transistor of the present invention will be described. The substrate material is not particularly limited, as long as it can be processed into plate shape, sheet shape or film shape, and examples thereof include silicon; inorganic glass such as quartz glass, soda glass, borosilicate glass or non alkali glass; and a resin or a polymer compound such as cellulose acetate propionate (CAP), cellulose triacetate (TAC), polyarylate (PAR), polyimide, polyethylene (PE), polyethylene terephthalate (PET), polyethylene naphthalate (PEN), polyether imide (PEI), polyether ether ketone (PEEK), polyether sulfone (PES), polypropylene (PP), polycarbonate (PC), polycycloolefin, polyphenylene sulfide (PPS) or polymethyl methacrylate (PMMA).

Among these, from a viewpoint of improving productivity of the transistor, an inorganic substrate such as a glass plate or a silicon wafer is preferable, and from a viewpoint of obtaining a flexible transistor, a glass sheet, a resin sheet, a plastic film or other flexible materials is preferable, and from a viewpoint of lowering weight and improving portability and shock resistance, in addition to flexibility, a resin sheet or a plastic film is more preferable.

Next, an electrode which is a constituent element of the transistor of the present invention will be described.

The material of the gate electrode, the source electrode and the drain electrode is not particularly limited, as long as it is a conductive material, and examples thereof include an inorganic conductive material and an organic conductive material.

Examples of the inorganic conductive material include lithium, beryllium, carbon, sodium, magnesium, aluminum, silicon, potassium, calcium, scandium, titanium, chromium, manganese, iron, nickel, copper, zinc, gallium, zirconium, niobium, molybdenum, silver, tin, antimony, hafnium, tungsten, platinum, gold, graphite, glassy carbon, tin oxide, indium tin oxide (ITO), fluorine-doped zinc oxide, sodium-potassium alloy, molybdenum-tantalum alloy, aluminum-aluminum oxide mixture, silver-silver oxide mixture, magnesium-aluminum mixture, magnesium-indium mixture, magnesium-silver mixture, magnesium-copper mixture, lithium-aluminum mixture, doped silicon, carbon paste, silver ink, silver paste, copper ink, copper paste, nanomaterial of silver, and nanomaterial of copper.

Meanwhile, examples of the organic conductive material include a conventionally known conductive polymer, in which electrical conductivity is improved by doping, such as conductive polyaniline, a conductive polyaniline derivative, conductive polypyrrole, a conductive polypyrrole derivative, conductive polythiophene, a conductive polythiophene derivative, a complex of polyethylene dioxythiophene and polystyrene sulfonic acid (PEDOT-PSS); and a charge transfer complex such as a tetrathiafulvalene-tetracyanoquinodimethane complex.

Each electrode may be formed of one kind of conductive material or may be formed of two or more kinds of conductive material. In a case of two or more kinds thereof, these may be used as a mixture or as a multilayer. In addition, regarding the gate electrode, the source electrode and the drain electrode, the same conductive material may be used or different materials may be used in the respective electrodes.

A thickness of the electrode is suitably determined within a range of achieving desired electrical conductivity according to the kind of the conductive material used for forming the electrode, and is generally preferably 1 nm to 1 µm, more preferably 10 nm to 200 nm, and even more preferably 20 nm to 100 nm.

The shapes of the source electrode and the drain electrodes are not particularly limited, as long as they are formed so as to oppose each other with a substantially certain gap, which corresponds to a channel length (L).

The channel length (L) is generally preferably 0.1 µm to 1 mm, more preferably 0.5 µm to 200 µm, and even more preferably 1 µm to 100 µm.

As a method of forming an electrode, a conventionally known method disclosed in Material Matters Basics, vol. 6 (Sigma-Aldrich Corporation) can be used, and the method is not particularly limited, as long as it is a method capable of allowing the formation of an electrode into desired shape (pattern) and desired thickness, and examples thereof include a method including the steps of first forming a conductive film all over the surface by using a wet film forming method or a dry film forming method, patterning a resist on the above conductive film by a photolithography or a printing method, and etching; a method including the step of patterning the above conductive film by laser ablation; a method including the step of directly patterning by a dry film forming method through a mask; and a method including the step of directly patterning by a printing method.

Examples of the dry film forming method include a chemical vapor deposition (CVD) method such as a plasma CVD method, a thermal CVD method or a laser CVD method; and a physical vapor deposition (PVD) method such as a vacuum deposition method, a sputtering method or an ion plating method, and examples of the wet film forming method include an electrolytic plating method, an immersion plating method, an electroless plating method, a sol-gel method, an organic metal decomposition (MOD) method, a coating method and a printing method.

Examples of the method performed through the mask include a metal mask method and a lift-off method, examples of the coating method include an electro spray deposition (ESD) method, an evaporative spray deposition from ultra-dilute solution (ESDUS) method, an air doctor coating method, an air knife coating method, an edge casting method, an impregnation coating method, a kiss coating method, a cast coating method, a squeeze coating method, a spin coating method, a slit coating method, an electrostatic coating method, an electrostatic spray coating method, a die coating method, an ultrasonic spray coating method, a supercritical spray coating method, a dispensing method, a dip coating method, a doctor blade coating method, a transfer roll coating method, a drop casting method, a bar coating method, a blade coating method, a reverse coating method, a roll coating method and a wire bar coating method, and examples of the printing method include an inkjet printing method, an offset printing method, a capillary pen printing method, a gravure printing method, a gravure offset printing method, a screen printing method, a dispensing method, a letterpress printing method, a reverse off-set printing method, a drop casting method, a flexographic printing method, a lithographic printing method and a microcontact printing method.

Among these, from a viewpoint of reducing manufacturing cost, a method using a wet film forming method, in which a vacuum environment is not necessary, is preferable, and among the wet film forming methods, a method using a printing method having the small number of steps is more preferable.

Next, the gate insulator which is a constituent element of the transistor of the present invention will be described.

The gate insulator has a function of electrically insulating the gate electrode and the source electrode, the gate electrode and the drain electrode, and the gate electrode and the semiconductor layer. Therefore, the material of the gate insulator is not particularly limited, as long as it is an electrical insulating material, and examples thereof include a polymer compound such as cyanoethyl pullulan, cellulose acetate propionate (CAP), cellulose triacetate (TAC), polyarylate (PAR), polyimide, polyester, polyethylene terephthalate (PET), polyethylene naphthalate (PEN), polyether imide (PEI), polyether ether ketone (PEEK), polyether sulfone (PES), polyvinylidene chloride (PVDC), polyvinyl chloride (PVC), polycarbonate (PC), polycycloolefin, polystyrene and a polystyrene derivative, polytetrafluoroethylene (PTFE), a polyparaxylylene derivative such as PARYLENE SERIES (product name), polyvinyl alcohol (PVA), polyvinyl phenol (PVP), polyphenylene sulfide (PPS), polymethyl methacrylate (PMMA), acrylic resin, amorphous fluororesin such as CYTOP SERIES (product name, Asahi Glass Co., Ltd.), alkyd resin, urethane resin, epoxy resin, an electron beam curable resin such as electron beam curable acrylic resin or electron beam curable methacrylic resin, phenol resin, polyimide resin, polyvinyl phenol resin, phenoxy resin, phenol resin, fluororesin, unsaturated polyester resin, melamine resin, or a UV curable resin such as UV curable acrylic resin or UV curable methacrylic resin; and an inorganic material such as $Al_2O_3$, $SiO_2$, $Ba_xSr_{(1-x)}TiO_3$ or $BaTi_xZr_{(1-x)}O_3$.

The gate insulator may be formed of one kind of insulating material or may be formed of two or more kinds of insulating materials. In addition, the gate insulator may include a reaction (polymerization) initiator, a crosslinking agent, a crosslinking aid, and the like.

In a case where the gate insulator is formed of two or more kinds of insulating materials, each insulating material may be simply mixed or a covalent bond may be formed between the insulating materials. In addition, in a case where a reaction (polymerization) initiator, a crosslinking agent or a crosslinking aid is included, these materials and the insulating material may be simply mixed or a covalent bond may be formed between these materials.

A thickness of the gate insulator is suitably determined within a range of achieving desired insulating properties according to the kind of the insulating material used for forming the gate insulator, and is generally preferably 10 nm to 5 μm.

The method of forming the gate insulator is not particularly limited, as long as it is possible to form a film (layer) capable of electrically insulating the gate electrode and the source electrode, the gate electrode and the drain electrode, and the gate electrode and the semiconductor layer, and examples thereof include a conventionally known dry film forming method and wet film forming method.

Examples of the dry film forming method include a chemical vapor deposition (CVD) method such as a plasma CVD method, a thermal CVD method or a laser CVD method; and a physical vapor deposition (PVD) method such as a vacuum deposition method, a sputtering method or an ion plating method, and examples of the wet film forming method include an electrolytic plating method, an immersion plating method, an electroless plating method, a sol-gel method, an organic metal decomposition (MOD) method, a coating method and a printing method.

Examples of the coating method include an electro spray deposition (ESD) method, an evaporative spray deposition from ultra-dilute solution (ESDUS) method, an air doctor coating method, an air knife coating method, an edge casting method, an impregnation coating method, a kiss coating method, a cast coating method, a squeeze coating method, a spin coating method, a slit coating method, an electrostatic coating method, an electrostatic spray coating method, a die coating method, an ultrasonic spray coating method, a supercritical spray coating method, a dispensing method, a dip coating method, a doctor blade coating method, a transfer roll coating method, a drop casting method, a bar coating method, a blade coating method, a reverse coating method, a roll coating method and a wire bar coating method, and examples of the printing method include an inkjet printing method, an offset printing method, a capillary pen printing method, a gravure printing method, a gravure offset printing method, a screen printing method, a dispensing method, a letterpress printing method, a reverse off-set printing method, a drop casting method, a flexographic printing method, a lithographic printing method and a microcontact printing method.

Among these, from a viewpoint of reducing manufacturing cost, a method using a wet film forming method, in which a vacuum environment is not necessary, is preferable.

In a case where the patterning is necessary, the patterning can be performed by the same method as disclosed in the section of "electrode".

The semiconductor layer which constitutes the transistor of the present invention will be described.

The transistor of the present invention is characterized in that the compound of the present invention is included in the semiconductor layer which constitutes the transistor. The semiconductor layer which constitutes the transistor of the present invention may include materials other than the compound of the present invention, as long as desired semiconductor properties can be exhibited. Examples of such materials include other semiconductor materials, a polymer compound or a resin, a body or extender pigment, a surfactant, a release agent, and other additive agents, which are described in the section of Ink of Present Invention.

A thickness of the semiconductor layer is suitably determined within a range of achieving desired semiconductor properties according to the kind of the semiconductor material used for forming the semiconductor layer, and is generally preferably in a range of 0.5 nm to 1 μm, more preferably in a range of 5 nm to 500 nm, and even more preferably in a range of 10 nm to 300 nm.

A method of forming the semiconductor layer is not particularly limited, as long as it is a method capable of allowing the formation of a semiconductor layer which covers at least a channel region which is between the source electrode and the drain electrode, and examples thereof include a conventionally known dry film forming method and wet film forming method.

Examples of the dry film forming method include a chemical vapor deposition (CVD) method such as a plasma CVD method, a thermal CVD method or a laser CVD method; and a physical vapor deposition (PVD) method such as a vacuum deposition method, a sputtering method or an ion plating method, and examples of the wet film forming method include a coating method such as an electro spray deposition (ESD) method, an evaporative spray deposition from ultra-dilute solution (ESDUS) method, an air doctor coating method, an air knife coating method, an edge casting method, an impregnation coating method, a kiss coating method, a cast coating method, a squeeze coating method, a spin coating method, a slit coating method, an electrostatic coating method, an electrostatic spray coating method, a die coating method, an ultrasonic spray coating method, a supercritical spray coating method, a dispensing method, a dip coating method, a doctor blade coating method, a transfer roll coating method, a drop casting method, a bar coating method, a blade coating method, a reverse coating method, a roll coating method and a wire bar coating method; and a printing method such as an inkjet printing method, an offset printing method, a capillary pen printing method, a gravure printing method, a gravure offset printing method, a screen printing method, a dispensing method, a letterpress printing method, a reverse off-set printing method, a drop casting method, a flexographic printing method, a lithographic printing method and a microcontact printing method.

Among these, from viewpoints of reducing manufacturing cost and decreasing a temperature of the manufacturing process, a method using a wet film forming method is preferable.

Regarding the formation of the semiconductor layer, if necessary, annealing may be performed after the layer is formed as described above, in order to improve the semiconductor properties by increasing crystallinity of the semiconductor material. A temperature of the annealing is preferably in a range of 50° C. to 200° C. and more preferably in a range of 70° C. to 200° C., and the time of the annealing is preferably in a range of 10 minutes to 12 hours, more preferably in a range of 1 hour to 10 hours and even more preferably in a range of 30 minutes to 10 hours.

The transistor of the present invention can be used as a switching transistor of the pixels of a display device, a signal driver circuit of a pixel configuring a display device, a memory circuit, a sensor circuit, an inverter, a ring oscillator or an RFID.

Examples of the display device include a liquid crystal display device, a dispersion type liquid crystal display device, an electrophoretic display device, a particle rotation display device, an electrochromic display device, an organic EL display device, and an electronic paper.

EXAMPLES

The present invention will be described in more detail with reference to Examples.

Example 1

<Preparation of Compound (101)>

The preparation of compound (101) will be described. Compound (101) is a compound represented by General Formula (1) in which Ar is a phenyl group and $R^1$ is a hexyl group.

[Chem. 12]

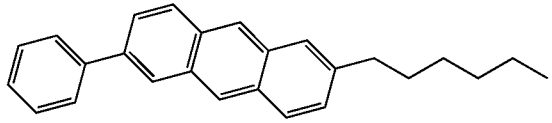

(101)

A synthetic scheme is shown in (S101).

[Chem. 13]

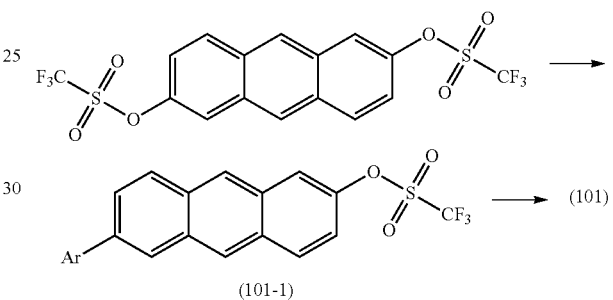

(S101)

First, the method of synthesizing compound (101-1) will be described. Under the argon atmosphere, 42 mL of dry cyclopentyl methyl ether and 4.2 mL of dry N, N-dimethylformamide were added to 2.5 g (5.3 mmol) of 2,6-bis (trifluoromethanesulfonyl) anthracene prepared by the method disclosed in NPL 1, 0.12 g (0.11 mmol) of tetrakis (triphenylphosphine) palladium (0), 1.7 g (7.9 mmol) of potassium phosphate, and 0.69 g (5.8 mmol) of potassium bromide, and the mixture was stirred at room temperature. After 0.64 g (5.3 mmol) of phenyl boronic acid was added to the reaction solution, the mixture was stirred at 100° C. for 16 hours. Chloroform was added to the reaction solution, followed by washing with water, the organic phase was dried with magnesium sulfate, and the solvent was removed under vacuum. The obtained crude product was recrystallized from acetone, and thereby 0.94 g of compound (101-1) (yield, 44%) was obtained.

Next, the method of synthesizing compound (101) will be described. Under argon atmosphere, 11.2 mL of dry tetrahydrofuran was added to 0.10 g (0.25 mmol) of compound (101-1) and 0.0066 g (0.012 mmol) of dichloro[1,3-bis (diphenylphosphino)propane]nickel (II), and the mixture was cooled to 0° C., to which 0.15 mL (0.30 mmol) of a 2 M ether solution of n-hexyl magnesium bromide was slowly added dropwise. The reaction solution was heated to room temperature and further stirred for 2 hours. The reaction was stopped by adding water to the reaction solution, and then the solvent was removed under vacuum. After addition of chloroform followed by washing with water, the organic phase was dried with magnesium sulfate and the solvent was removed under vacuum. The obtained crude product was purified by silica gel column chromatography (cyclohexane), and thereby 43 mg of compound (101) (yield, 51%) was obtained.

$^1$H-NMR (400 MHz, CDCl$_3$): δ8.43 (s, 1H), δ8.35 (s, 1H), δ8.18 (s, 1H), δ8.06 (d, J=8.8 Hz, 1H), δ7.94 (d, J=8.8 Hz, 1H), δ7.79-7.72 (m, 4H), δ7.53-7.48 (m, 2H), δ7.40-7.33 (m, 2H), δ2.81 (t, J=7.6 Hz, 2H), δ1.78-1.72 (m, 2H), δ1.45-1.29 (m, 6H), δ0.90 (t, J=7.0 Hz, 3H)

<Solubility of Compound (101)>

Solubility was evaluated by completely dissolving compound (101) visually by adding p-xylene at room temperature (25° C.). The result is shown in Table 1.

<Fabrication of Transistor with Compound (101)>

A glass substrate was subjected to ultrasonic cleaning with a neutral detergent aqueous solution, distilled water, acetone and ethanol in this order (each 30 min×3 times), a platinum gate electrode (thickness: 30 nm) was pattern-deposited on the glass substrate by sputtering through a shadow metal mask, and a gate insulator (thickness: 1 μm) made of a dichloro-di-p-xylylene polymer (polyparaxylylene) was formed over the gate electrode by thermal CVD. Then, on the gate insulator, gold source and drain electrodes were deposited through a shadow metal mask by vacuum evaporation (2×10$^{-6}$ Torr) with a thickness of 20 nm, a channel length of 75 μm, and a channel width of 3000 μm). Next, this substrate was immersed in an ethanol solution of pentafluorobenzenethiol (concentration: 0.08 wt %) for 1 hour and then rinsed with ethanol. Finally, 0.05 μL of a p-xylene solution (0.4 wt %) of compound (101) was drop casted over the source and drain electrodes followed by drying at room temperature, to form a semiconductor layer.

<Mobility of Transistor with Compound (101)>

Under a state where −80 V was applied to the drain electrode of the common source, the current (I$_d$) flowing into the drain electrode was measured while the voltage (V$_g$) applied to the gate electrode was swept from +40 V to −60 V. The mobility of the transistor fabricated as described above was calculated in units of cm$^2$/Vs from the slope of $\sqrt{I_d}$—V$_g$ using the equation (Eq. 101).

[Equation 1]

$$I_d = (W/2L)C\mu(V_g - V_T)^2 \quad \text{(Eq. 101)}$$

In the equation, W represents the channel width, L represents the channel length, μ represents the mobility, C represents the capacitance per area of the gate insulator, and V$_T$ represents the threshold voltage. The result is shown in Table 2.

Example 2

<Preparation of Compound (102)>

The preparation of compound (102) will be described. The compound (102) is a compound represented by General Formula (1) in which Ar is a phenyl group and R$^1$ is a heptyl group.

[Chem. 14]

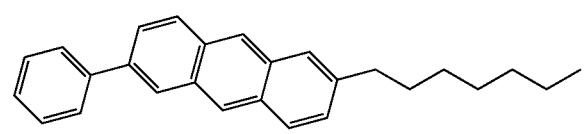

(102)

Compound (102) was obtained in the same manner as in Example 1, except that n-heptyl magnesium bromide was used instead of n-hexyl magnesium bromide in Example 1.

$^1$H-NMR (400 MHz, CDCl$_3$): δ8.43 (s, 1H), δ8.35 (s, 1H), δ8.18 (s, 1H), δ8.06 (d, J=8.8 Hz, 1H), δ7.94 (d, J=8.8 Hz, 1H), δ7.79-7.72 (m, 4H), δ7.51 (t, J=7.8 Hz, 2H), δ7.41-7.32 (m, 2H), δ2.81 (t, J=7.6 Hz, 2H), δ1.79-1.71 (m, 2H), δ1.38-1.28 (m, 8H), δ0.89 (t, J=7.0 Hz, 3H)

<Solubility of Compound (102)>

The solubility was evaluated in the same manner as in Example 1, except that compound (102) was used instead of compound (101) in Example 1. The result is shown in Table 1.

<Fabrication of Transistor with Compound (102)>

A transistor was fabricated in the same manner as in Example 1, except that the compound (102) was used instead of the compound (101) in Example 1.

<Mobility of Transistor with Compound (102)>

The mobility of the transistor was characterized in the same manner as in Example 1, except that the transistor fabricated using compound (102) was used instead of the transistor fabricated using compound (101) in Example 1. The result is shown in Table 2.

Example 3

<Preparation of Compound (103)>

The preparation of compound (103) will be described. Compound (103) is a compound represented by General Formula (1) in which Ar is a phenyl group and R$^1$ is an octyl group.

[Chem. 15]

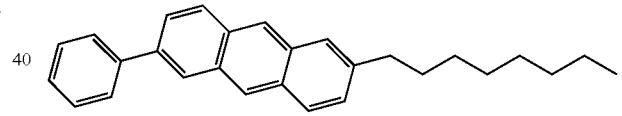

(103)

Compound (103) was obtained in the same manner as in Example 1, except that n-octyl magnesium bromide was used instead of n-hexyl magnesium bromide in Example 1.

$^1$H-NMR (400 MHz, CDCl$_3$): δ8.43 (s, 1H), δ8.35 (s, 1H), δ8.18 (s, 1H), δ8.06 (d, J=8.8 Hz, 1H), δ7.94 (d, J=8.8 Hz, 1H), δ7.80-7.73 (m, 4H), δ7.51 (t, J=7.8 Hz, 2H), δ7.41-7.33 (m, 2H), δ2.81 (t, J=7.6 Hz, 2H), δ1.75-1.73 (m, 2H), δ1.37-1.28 (m, 10H), δ0.88 (t, J=7.2 Hz, 3H)

<Solubility of Compound (103)>

The solubility was evaluated in the same manner as in Example 1, except that compound (103) was used instead of compound (101) in Example 1. The result is shown in Table 1.

<Fabrication of Transistor with Compound (103)>

The transistor was fabricated in the same manner as in Example 1, except that compound (103) was used instead of compound (101) in Example 1.

<Mobility of Transistor with Compound (103)>

The mobility of the transistor was evaluated in the same manner as in Example 1, except that the transistor fabricated using compound (103) was used instead of the transistor fabricated using compound (101) in Example 1. The result is shown in Table 2.

Example 4

<Preparation of Compound (104)>

Preparation of compound (104) will be described. Compound (104) is a compound represented by General Formula (1) in which Ar is a phenyl group and $R^1$ is a nonyl group.

[Chem. 16]

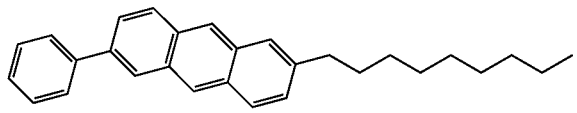

(104)

Compound (104) was obtained in the same manner as in Example 1, except that n-nonyl magnesium bromide was used instead of n-hexyl magnesium bromide in Example 1.

$^1$H-NMR (400 MHz, CDCl$_3$): δ8.43 (s, 1H), δ8.35 (s, 1H), δ8.18 (s, 1H), δ8.06 (d, J=8.8 Hz, 1H), δ7.94 (d, J=8.8 Hz, 1H), δ7.79-7.72 (m, 4H), δ7.51 (t, J=7.8 Hz, 2H), δ7.41-7.26 (m, 2H), δ2.80 (t, J=7.7 Hz, 2H), δ1.76-1.71 (m, 2H), δ1.54-1.27 (m, 12H), δ0.88 (t, J=6.8 Hz, 3H)

<Solubility of Compound (104)>

The solubility was evaluated in the same manner as in Example 1, except that compound (104) was used instead of compound (101) in Example 1. The result is shown in Table 1.

<Fabrication of Transistor with Compound (104)>

The transistor was fabricated in the same manner as in Example 1, except that compound (104) was used instead of compound (101) in Example 1.

<Mobility of Transistor with Compound (104)>

The mobility of the transistor was evaluated in the same manner as in Example 1, except that the transistor fabricated using compound (104) was used instead of the transistor fabricated using compound (101) in Example 1. The result is shown in Table 2.

Example 5

<Preparation of Compound (105)>

Preparation of compound (105) will be described. Compound (105) is a compound represented by General Formula (1) in which Ar is a phenyl group and $R^1$ is a decyl group.

[Chem. 17]

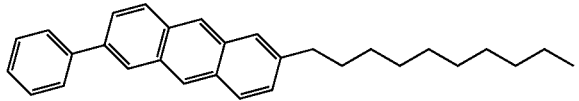

(105)

Compound (105) was obtained in the same manner as in Example 1, except that n-decyl magnesium bromide was used instead of n-hexyl magnesium bromide in Example 1.

$^1$H-NMR (400 MHz, CDCl$_3$): δ8.43 (s, 1H), δ8.36 (s, 1H), δ8.18 (s, 1H), δ8.06 (d, J=8.8 Hz, 1H), δ7.94 (d, J=8.8 Hz, 1H), δ7.79-7.72 (m, 4H), δ7.54-7.48 (m, 2H), δ7.39-7.33 (m, 2H), δ2.81 (t, J=7.6 Hz, 2H), δ1.77-1.71 (m, 2H), δ1.46-1.24 (m, 14H), δ0.88 (t, J=7.0 Hz, 3H)

<Solubility of Compound (105)>

The solubility was evaluated in the same manner as in Example 1, except that compound (105) was used instead of compound (101) in Example 1. The result is shown in Table 1.

<Fabrication of Transistor with Compound (105)>

The transistor was fabricated in the same manner as in Example 1, except that compound (105) was used instead of compound (101) in Example 1.

<Mobility of Transistor with Compound (105)>

The mobility of the transistor was evaluated in the same manner as in Example 1, except that the transistor fabricated using compound (105) was used instead of the transistor fabricated using compound (101) in Example 1. The result is shown in Table 2.

Example 6

<Preparation of Compound (106)>

Preparation of compound (106) will be described. Compound (106) is a compound represented by General Formula (1) in which Ar is a 4-methylphenyl group and $R^1$ is a hexyl group.

[Chem. 18]

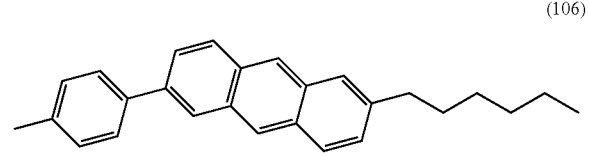

(106)

Compound (106) was obtained in the same manner as in Example 1, except that 4-methylphenylboronic acid was used instead of phenylboronic acid in Example 1.

$^1$H-NMR (400 MHz, CDCl$_3$): δ8.40 (s, 1H), δ8.33 (s, 1H), δ8.14 (s, 1H), δ8.03 (d, J=9.6 Hz, 1H), δ7.92 (d, J=8.8 Hz, 1H), δ7.74-7.71 (m, 2H), δ7.66 (d, J=7.6 Hz, 2H), δ7.33-7.27 (m, 3H), δ2.80 (t, J=7.8 Hz, 2H), δ2.42 (s, 3H), δ1.76-1.70 (m, 2H), δ1.40-1.29 (m, 8H), δ0.88 (t, J=7.2 Hz, 3H)

<Solubility of Compound (106)>

The solubility was evaluated in the same manner as in Example 1, except that compound (106) was used instead of compound (101) in Example 1. The result is shown in Table 1.

<Fabrication of Transistor with Compound (106)>

The transistor was fabricated in the same manner as in Example 1, except that compound (106) was used instead of compound (101) in Example 1.

<Mobility of Transistor with Compound (106)>

The mobility of the transistor was evaluated in the same manner as in Example 1, except that the transistor fabricated using compound (106) was used instead of the transistor fabricated using compound (101) in Example 1. The result is shown in Table 2.

Example 7

<Preparation of Compound (107)>

The preparation of compound (107) will be described. Compound (107) is a compound represented by General Formula (1) in which Ar is a 4-methylphenyl group and $R^1$ is a decyl group.

[Chem. 19]

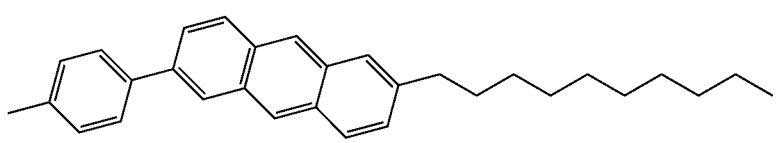

(107)

Compound (107) was obtained in the same manner as in Example 1, except that 4-Methylphenylboronic acid was used instead of phenylboronic acid in Example 1, and n-decylmagnesium bromide was used instead of n-hexylmagnesium bromide in Example 1.

$^1$H-NMR (400 MHz, CDCl$_3$): δ8.40 (s, 1H), δ8.32 (s, 1H), δ8.14 (s, 1H), δ8.03 (d, J=8.8 Hz, 1H), δ7.92 (d, J=8.8 Hz, 1H), δ7.74-7.70 (m, 2H), δ7.66 (d, J=8.4 Hz, 2H), δ7.33-7.27 (m, 3H), δ2.79 (t, J=7.8 Hz, 2H), δ2.42 (s, 3H), δ1.77-1.69 (m, 2H), δ1.42-1.29 (m, 14H), δ0.86 (t, J=6.8 Hz, 3H)

<Solubility of Compound (107)>

The solubility was evaluated in the same manner as in Example 1, except that compound (107) was used instead of compound (101) in Example 1. The result is shown in Table 1.

<Fabrication of Transistor with Compound (107)>

The transistor was fabricated in the same manner as in Example 1, except that compound (107) was used instead of compound (101) in Example 1.

<Mobility of Transistor with Compound (107)>

The mobility of the transistor was evaluated in the same manner as in Example 1, except that the transistor fabricated using compound (107) was used instead of the transistor fabricated using compound (101) in Example 1. The result is shown in Table 2.

Comparative Example 1

<Preparation of Compound (C101)>

Compound (C101) was obtained by the method disclosed in NPL 1.

[Chem. 20]

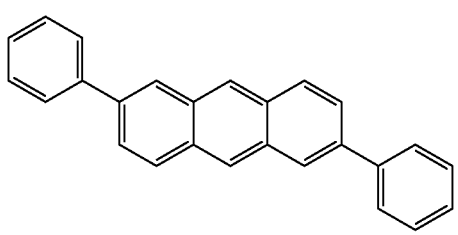

(C101)

<Solubility of Compound (C101)>

The solubility was evaluated in the same manner as in Example 1, except that compound (C101) was used instead of compound (101) in Example 1. The result is shown in Table 1.

<Fabrication of Transistor with Compound (C101)>

The transistor was fabricated in the same manner as in Example 1, except that compound (C101) was used instead of compound (101) in Example 1.

<Mobility of Transistor with Compound (C101)>

The mobility of the transistor was evaluated in the same manner as in Example 1, except that the transistor fabricated using compound (C101) was used instead of the transistor fabricated using compound (101) in Example 1. The result is shown in Table 2.

Comparative Example 2

<Preparation of Compound (C102)>

Compound (C102) was obtained by the method disclosed in Chemistry of Materials, 2015, vol. 27, p. 3809.

[Chem. 21]

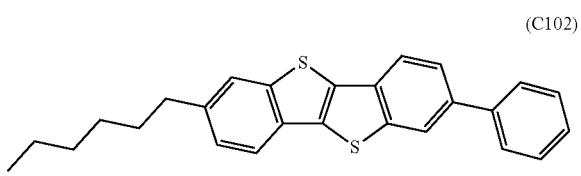

(C102)

<Fabrication of Transistor with Compound (C102)>

The transistor was fabricated in the same manner as in Example 1, except that compound (C102) was used instead of compound (101) in Example 1.

<Mobility of Transistor with Compound (C102)>

The mobility of the transistor was evaluated in the same manner as in Example 1, except that the transistor fabricated using compound (C102) was used instead of the transistor fabricated using compound (101) in Example 1. The result is shown in Table 2.

Comparative Example 3

<Preparation of Compound (C103)>

Compound (C103) was obtained in the same manner as in Comparative Example 2.

[Chem. 22]

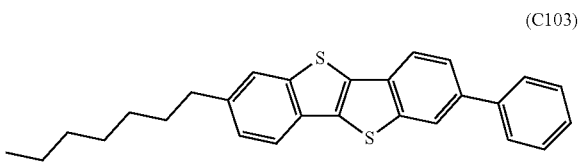

(C103)

<Fabrication of Transistor with Compound (C103)>

The transistor was fabricated in the same manner as in Example 1, except that compound (C103) was used instead of compound (101) in Example 1.

<Mobility of Transistor with Compound (C103)>

The mobility of the transistor was evaluated in the same manner as in Example 1, except that the transistor fabricated using compound (C103) was used instead of the transistor fabricated using compound (101) in Example 1. The result is shown in Table 2.

Comparative Example 4

<Preparation of Compound (C104)>

Compound (C104) was obtained in the same manner as in Comparative Example 2.

[Chem. 23]

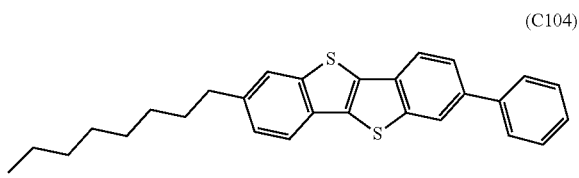

(C104)

<Fabrication of Transistor with Compound (C104)>

The transistor was fabricated in the same manner as in Example 1, except that compound (C104) was used instead of compound (101) in Example 1.

<Mobility of Transistor with Compound (C104)>

The mobility of the transistor was evaluated in the same manner as in Example 1, except that the transistor fabricated using compound (C104) was used instead of the transistor fabricated using compound (101) in Example 1. The result is shown in Table 2.

Comparative Example 5

<Preparation of Compound (C105)>

Compound (C105) was obtained in the same manner as in Comparative Example 2.

[Chem. 24]

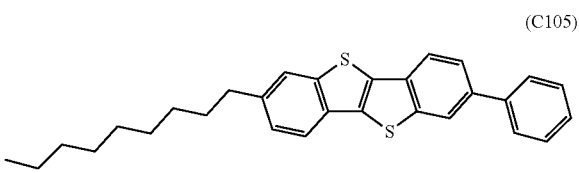

(C105)

<Fabrication of Transistor with Compound (C105)>

The transistor was fabricated in the same manner as in Example 1, except that compound (C105) was used instead of compound (101) in Example 1.

<Mobility of Transistor with Compound (C105)>

The mobility of the transistor was evaluated in the same manner as in Example 1, except that the transistor fabricated using compound (C105) was used instead of the transistor fabricated using compound (101) in Example 1. The result is shown in Table 2.

Comparative Example 6

<Preparation of Compound (C106)>

Compound (C106) was obtained in the same manner as in Comparative Example 2.

[Chem. 25]

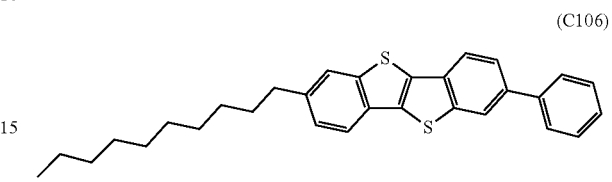

(C106)

<Fabrication of Transistor with Compound (C106)>

The transistor was fabricated in the same manner as in Example 1, except that compound (C106) was used instead of compound (101) in Example 1.

<Mobility of Transistor with Compound (C106)>

The mobility of the transistor was evaluated in the same manner as in Example 1, except that the transistor fabricated using compound (C106) was used instead of the transistor fabricated using compound (101) in Example 1. The result is shown in Table 2.

Comparative Example 7

<Preparation of Compound (C107)>

Compound (C107) was obtained in the same manner as in Comparative Example 2.

[Chem. 26]

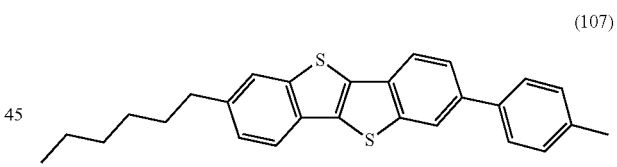

(107)

<Fabrication of Transistor with Compound (C107)>

The transistor was fabricated in the same manner as in Example 1, except that compound (C107) was used instead of compound (101) in Example 1.

<Mobility of Transistor with Compound (C107)>

The mobility of the transistor was evaluated in the same manner as in Example 1, except that the transistor fabricated using compound (C107) was used instead of the transistor fabricated using compound (101) in Example 1. The result is shown in Table 2.

Comparative Example 8

<Preparation of Compound (C108)>

Compound (C108) was obtained in the same manner as in Comparative Example 2.

[Chem. 27]

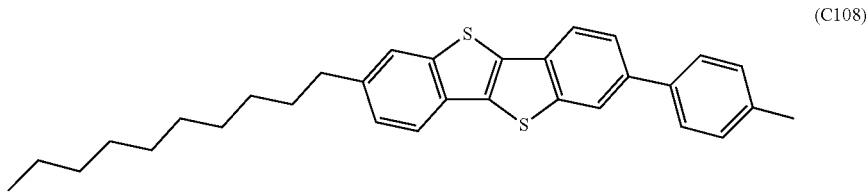

(C108)

<Fabrication of Transistor with Compound (C108)>

The transistor was fabricated in the same manner as in Example 1, except that compound (C108) was used instead of compound (101) in Example 1.

<Mobility of Transistor with Compound (C108)>

The mobility of the transistor was evaluated in the same manner as in Example 1, except that the transistor fabricated using compound (C108) was used instead of the transistor fabricated using compound (101) in Example 1. The result is shown in Table 2.

TABLE 1

| | Compound | Solubility of compound (wt %) |
|---|---|---|
| Example 1 | (101) | 1.3 |
| Example 2 | (102) | 1.1 |
| Example 3 | (103) | 0.7 |
| Example 4 | (104) | 0.7 |
| Example 5 | (105) | 0.4 |
| Example 6 | (106) | 0.8 |
| Example 7 | (107) | 0.4 |
| Comparative Example 1 | (C101) | <0.1 (which cannot accurately be evaluated due to low solubility) |

TABLE 2

| | Compound | Mobility ($cm^2/Vs$) |
|---|---|---|
| Example 1 | (101) | 1.2 |
| Example 2 | (102) | 2.4 |
| Example 3 | (103) | 3.3 |
| Example 4 | (104) | 1.7 |
| Example 5 | (105) | 2.1 |
| Example 6 | (106) | 2.3 |
| Example 7 | (107) | 1.4 |
| Comparative Example 1 | (C101) | Semiconductor layer cannot be formed due to significantly low solubility in p-xylene |
| Comparative Example 2 | (C102) | 0.5 |
| Comparative Example 3 | (C103) | 0.6 |
| Comparative Example 4 | (C104) | 0.5 |
| Comparative Example 5 | (C105) | 0.3 |
| Comparative Example 6 | (C106) | 0.1 |
| Comparative Example 7 | (C107) | 0.5 |
| Comparative Example 8 | (C108) | 0.3 |

As apparent from Table 1, the compound of the present invention exhibits high solvent solubility, compared to the compound (described in Comparative Example 1) disclosed in NPL 1. The higher the solubility, the more suitable to ink and the more industrially superior.

Table 2 indicates that the transistor having a semiconductor layer formed by a drop casting method using the compound of the present invention exhibits a high mobility equal to or greater than 1 $cm^2/Vs$. Among the wet film forming methods, the drop casting method correlates with an ink jet method, and is a method with high practicability. In contrast, the mobility of the transistor fabricated by the same method using the compound of the comparative example is low. Regarding the compound of the comparative example, it is difficult to form a film by drop casting due to its low solvent solubility.

INDUSTRIAL APPLICABILITY

The compound of the present invention has an anthracene skeleton and an appropriate substituent introduced to an appropriate position of the anthracene skeleton, and thus possesses both semiconductor properties and good solubility. Therefore, the compound of the present invention can be used as a semiconductor capable of being formed by a practical wet film forming method, and can be used for a semiconductor device having the semiconductor as a semiconductor layer.

REFERENCE SIGNS LIST

1: Substrate
2: Gate electrode
3: Gate insulator
4: Semiconductor layer
5: Source electrode
6: Drain electrode

The invention claimed is:

1. A compound represented by General Formula (1), exclusive of compound (1-1) below,

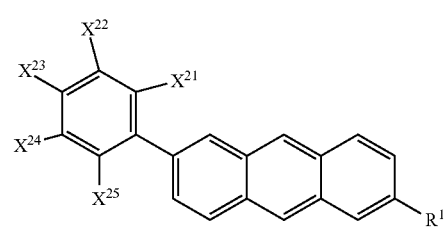

(1)

wherein $X^{21}$ to $X^{25}$ represent a hydrogen atom or an acyclic or cyclic alkyl group having 1 to 20 carbon atoms, and $R^1$ represents an acyclic alkyl group having 1 to 20 carbon atoms,

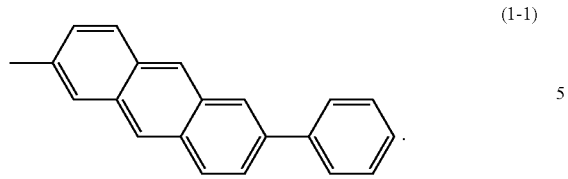

(1-1)

2. A semiconductor material comprising the compound according to claim 1.

3. An ink comprising the compound according to claim 1.

4. A semiconductor film comprising the compound according to claim 1.

5. A semiconductor device comprising a semiconductor layer comprising the compound according to claim 1.

6. A transistor comprising a semiconductor layer comprising the compound according to claim 1.

* * * * *